(12) United States Patent
Yun et al.

(10) Patent No.: US 7,527,913 B2
(45) Date of Patent: *May 5, 2009

(54) PHOTOACID GENERATORS, PHOTORESIST COMPOSITION INCLUDING THE SAME AND METHOD OF FORMING PATTERN USING THE SAME

(75) Inventors: Hyo-Jin Yun, Anyang-si (KR); Young-Gil Kwon, Anyang-si (KR); Young-Ho Kim, Yongin-si (KR); Do-Young Kim, Seoul (KR); Jae-Hee Choi, Bucheon-si (KR); Se-Kyung Baek, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/011,226

(22) Filed: Jan. 24, 2008

(65) Prior Publication Data

US 2008/0182203 A1    Jul. 31, 2008

(30) Foreign Application Priority Data

Jan. 25, 2007    (KR) .................... 10-2007-0007917

(51) Int. Cl.
*G03F 7/004* (2006.01)
*G03F 7/30* (2006.01)
*C07C 69/00* (2006.01)

(52) U.S. Cl. .................... 430/270.1; 430/313; 430/326; 430/910; 430/921; 430/922; 560/129; 560/150

(58) Field of Classification Search ............ 430/270.1, 430/313, 326, 922, 910, 921; 560/129, 150
See application file for complete search history.

(56) References Cited

U.S. PATENT DOCUMENTS

| | | | | |
|---|---|---|---|---|
| 7,262,321 | B2 * | 8/2007 | Harada et al. | ............... 560/129 |
| 2008/0182203 | A1 * | 7/2008 | Yun et al. | ................ 430/281.1 |

FOREIGN PATENT DOCUMENTS

| | | |
|---|---|---|
| JP | 2000-292917 | 10/2000 |
| JP | 2003-173023 | 6/2003 |
| JP | 2005-041857 | 2/2005 |

* cited by examiner

*Primary Examiner*—John S Chu
(74) *Attorney, Agent, or Firm*—Mills & Onello LLP

(57) ABSTRACT

A photoresist composition includes about 4% to about 10% by weight of a photoresist resin, about 0.1% to about 0.5% by weight of a photoacid generator having a sulfonium-salt cationic group and a sulfonium-salt anionic group containing a carboxyl group as a hydrophilic site and a remainder of a solvent. The photoresist composition may form a photoresist pattern having a uniform profile.

13 Claims, 4 Drawing Sheets

PHOTOACID GENERATORS, PHOTORESIST COMPOSITION INCLUDING THE SAME AND METHOD OF FORMING PATTERN USING THE SAME

CROSS-REFERENCE TO RELATED APPLICATIONS

This application claims priority under 35 U.S.C. § 119 to Korean Patent Application No. 2007-7917, filed on Jan. 25, 2007, in the Korean Intellectual Property Office (KIPO), the contents of which are herein incorporated by reference in their entirety.

FIELD OF THE INVENTION

Exemplary embodiments of the present invention relate to photoacid generators, photoresist compositions including the photoacid generators and methods of forming a pattern using the photoresist compositions. For example, certain embodiments of the present invention relate to photoacid generators capable of being used to form a pattern having a uniform profile on a substrate, photoresist compositions including the photoacid generators and methods of forming a pattern using the photoresist compositions.

BACKGROUND

Nowadays, semiconductor devices having higher degrees of integration are in high demand. Thus, active research is being conducted on methods of forming a fine pattern having a line width equal to or less than 100 nm. The fine pattern may be formed through a photolithography process using a photoresist having photosensitive characteristics.

The photolithography process typically includes a step of forming a photoresist film, a step of aligning/exposing the photoresist film and a step of developing the photoresist film so as to form a photoresist pattern. In the step of forming the photoresist film, a photoresist, the molecular structure of which may be changed by light, is coated on a substrate to form the photoresist film. In the step of aligning/exposing the photoresist film, a mask having a circuit pattern is aligned on the photoresist film formed on the substrate. Thereafter, light having an image of the circuit pattern of the mask is irradiated onto the photoresist film to generate a photochemical reaction. Irradiation causes the molecular structure of the exposed portions of the photoresist film to selectively change. Thereafter, the photoresist film is developed to form the photoresist pattern on the substrate.

In the step of developing the photoresist film, the photoresist film exposed to light is selectively removed or remains to form the photoresist pattern having a shape corresponding to the circuit pattern. The resolution of the photoresist pattern may be represented by the following Formula 1.

$R = k1 \lambda / NA$ ($R$: maximum resolution, $\lambda$: wavelength, $k1$: constant, $NA$: numerical aperture of a lens) <Formula 1>

As the wavelength of the light used for the step of exposing is decreased, the resolution of the photoresist pattern is improved, and the line width of the photoresist pattern is reduced. Thus, the minimum possible wavelength of the light, an exposing device based on the wavelength, and the maximum resolution of the photoresist may be considered important in forming a fine pattern having a nanoscale resolution.

The photoresist may be classified as either a negative photoresist or a positive photoresist. In the case of the positive photoresist, a cured portion of the photoresist film depends on a separation reaction of a blocking group due to an acid generated by a photoacid generator. For example, the acid generated by the photoacid generator is used for separating a specific blocking group, which is combined with a resin of the photoresist film, from the resin. Thus, the resin, from which the blocking group is separated, is changed to be easily dissolved in a developing solution in the subsequent developing process.

When a photoresist for argon fluoride (ArF), which is used for forming a pattern having a line width equal to or less than 75 nm, is used for forming a pattern, a manufacturing margin of an iso-dense pattern may not be sufficient. An insufficient manufacturing margin of the iso-dense pattern may cause a substantial difference between an actual critical dimension and a desired critical dimension in a peripheral area where pattern density is low compared to a cell area. In order to prevent and/or to reduce the above-mentioned problems, the amount of a photoacid generator may be increased. However, the photoresist pattern may be damaged so that an upper portion of the photoresist pattern may have a round shape. Furthermore, the photoacid generator may have hydrophobic characteristics so that the photoacid generator is not easily mixed with the resin having hydrophilic characteristics. Thus, the photoacid generator may not be uniformly distributed.

For example, referring to FIG. 1, a photoacid generator 14 of a photoresist film 10 has different characteristics from a resin 12. Thus, the photoacid generator 14 is not found near the resin 12, and adheres to each other in an upper portion of the photoresist film 10. Thus, a path, through which an acid generated by the photoacid generator 14 diffuses, is increased so that a photoresist pattern formed from the photoresist film 10 may not have a uniform profile.

SUMMARY OF THE INVENTION

Exemplary embodiments of the present invention provide photoacid generators having hydrophilic characteristics and capable of being distributed in a photoresist film.

Exemplary embodiments of the present invention also provide photoresist compositions including the photoacid generators described herein.

Exemplary embodiments of the present invention also provide methods of forming pattern, the methods being capable of improving critical line width margins and forming a pattern having a uniform profile.

According to one aspect of the present invention, a photoacid generator has a sulfonium-salt cationic group selected from the group consisting of compounds represented by the following Chemical Formulas 1, 2, 3 and 4 and a sulfonium-salt anionic group represented by the following Chemical Formula 5 and containing a carboxyl group as a hydrophilic site.

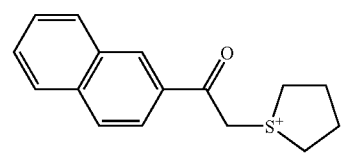

<Chemical Formula 1>

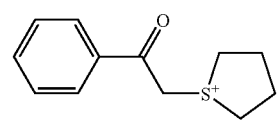

<Chemical Formula 2>

-continued

<Chemical Formula 3>

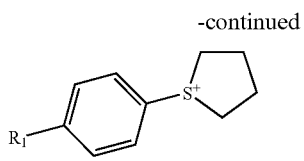

<Chemical Formula 4>

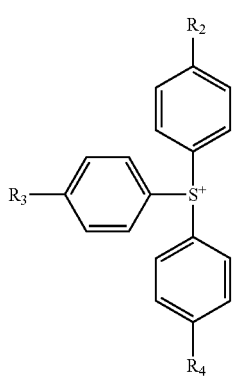

<Chemical Formula 5>

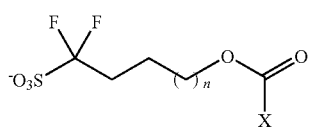

<Chemical Formula 6>

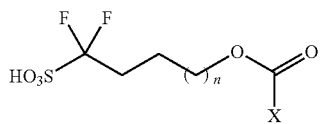

In Chemical Formulas 1 to 5, $R_1$, $R_2$, $R_3$ and $R_4$ independently represent a hydrogen atom or an alkyl group having 1 to 5 carbon atoms, n represents a natural number of 1 to 3, and X represents one selected from the group consisting of a cyclic group having 4 to 10 carbon atoms, an adamantyl group and a cycloheptyl group containing an oxygen atom.

According to another aspect of the present invention, a photoresist composition includes about 4% to about 10% by weight of a photoresist resin, about 0.1% to about 0.5% by weight of a photoacid generator having a sulfonium-salt cationic group and a remainder of a solvent. The photoacid generator contains one selected from the group consisting of compounds represented by Chemical Formulas 1, 2, 3 and 4 and a sulfonium-salt anionic group being represented by Chemical Formula 5 and containing a carboxyl group as a hydrophilic site.

According to another aspect of the present invention, a method of forming a pattern is provided. A photoresist composition is coated on an object layer to form a photoresist film. The photoresist composition includes about 4% to about 10% by weight of a photoresist resin, about 0.1% to about 0.5% by weight of a photoacid generator having a sulfonium-salt cationic group and a remainder of a solvent. The photoacid generator contains one selected from the group consisting of compounds represented by Chemical Formulas 1, 2, 3 and 4 and a sulfonium-salt anionic group being represented by Chemical Formula 5 and containing a carboxyl group as a hydrophilic site. The photoresist film is exposed to light. The photoresist film is developed to form a photoresist pattern. An exposed portion of the object layer is etched by using the photoresist pattern as an etching mask. Accordingly, an object layer pattern having a uniform profile may be formed.

For example, the photoacid generator may be reacted with light to generate a sulfonic acid represented by the following Chemical Formula 6.

In Chemical Formula 6, n presents a natural number of 1 to 3, and X may represent a cyclic group having 4 to 10 carbon atoms, an adamantyl group, a cycloheptyl group containing an oxygen atom, etc.

For example, the photoacid generator may be represented by the following Chemical Formulas 1-1, 1-2, 2-1, 2-2, 3-1, 3-2, 4-1 or 4-2. In Chemical Formulas 1-1, 1-2, 2-1, 2-2, 3-1, 3-2, 4-1 or 4-2, n represents a natural number of 1 to 3, and $R_1$, $R_2$, $R_3$ and $R_4$ independently represent a hydrogen atom or an alkyl group having 1 to 5 carbon atoms.

<Chemical Formula 1-1>

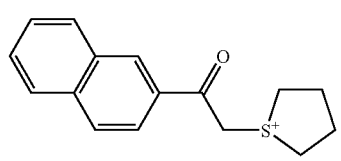

<Chemical Formula 1-2>

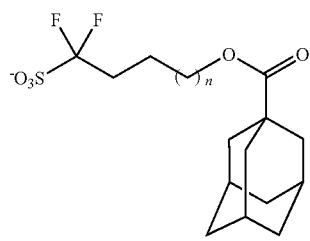

<Chemical Formula 2-1>

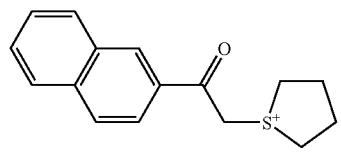

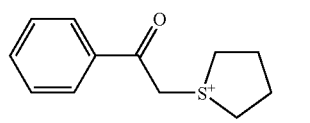

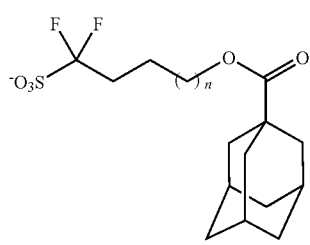

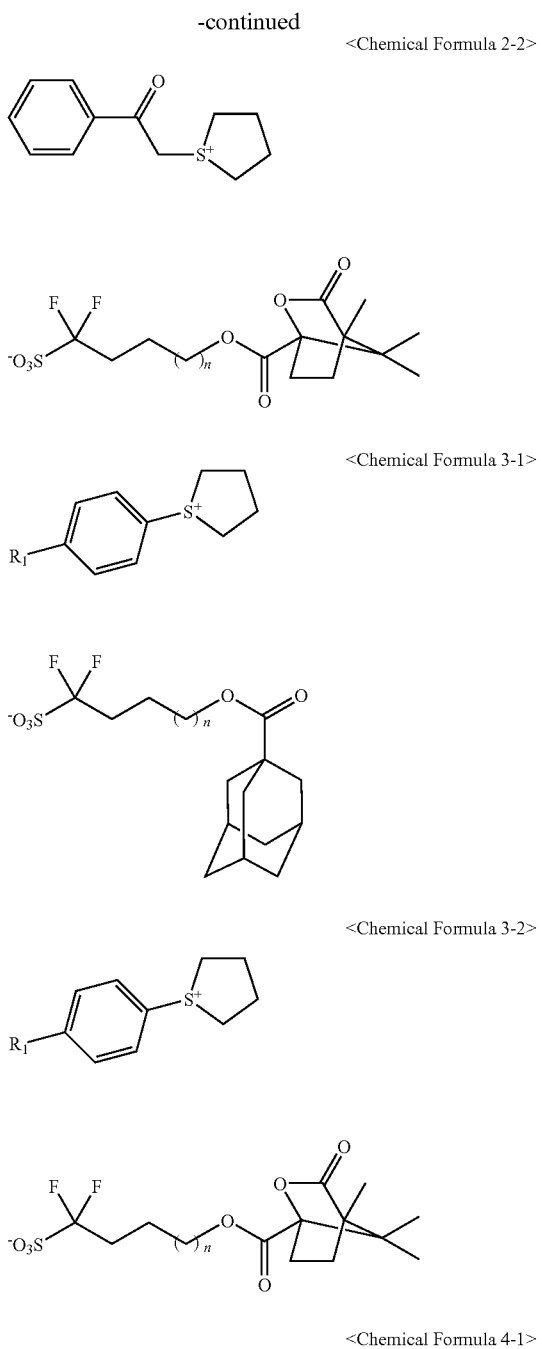
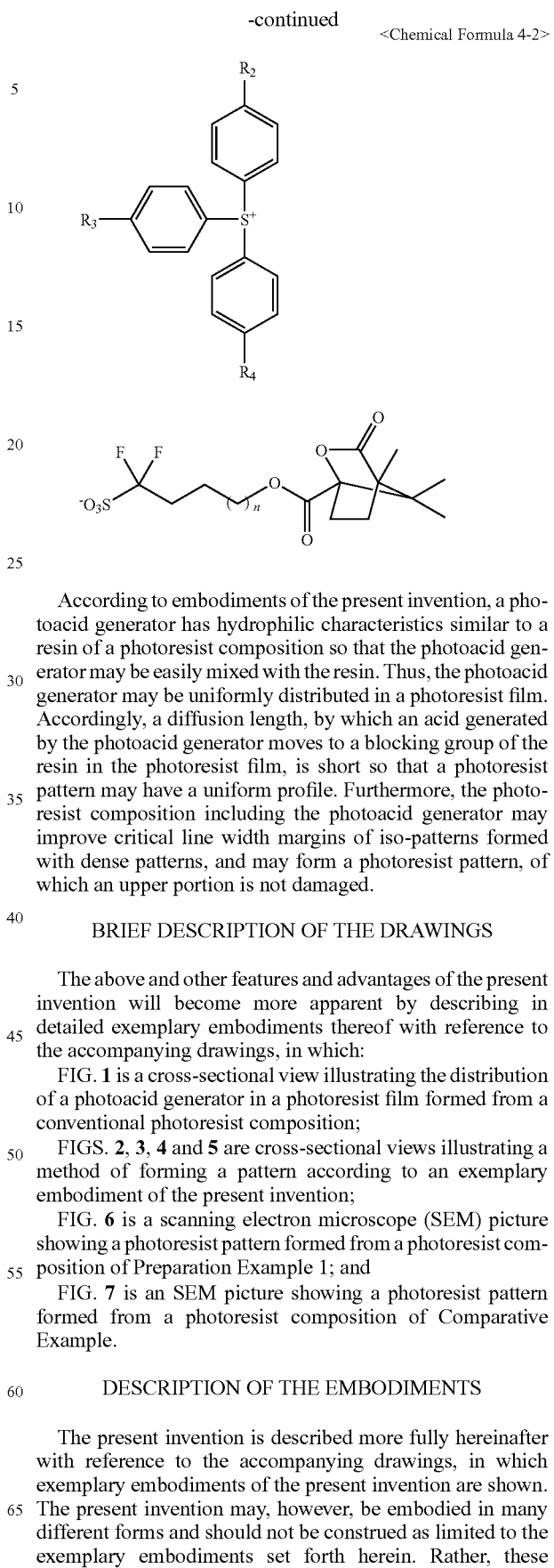

According to embodiments of the present invention, a photoacid generator has hydrophilic characteristics similar to a resin of a photoresist composition so that the photoacid generator may be easily mixed with the resin. Thus, the photoacid generator may be uniformly distributed in a photoresist film. Accordingly, a diffusion length, by which an acid generated by the photoacid generator moves to a blocking group of the resin in the photoresist film, is short so that a photoresist pattern may have a uniform profile. Furthermore, the photoresist composition including the photoacid generator may improve critical line width margins of iso-patterns formed with dense patterns, and may form a photoresist pattern, of which an upper portion is not damaged.

BRIEF DESCRIPTION OF THE DRAWINGS

The above and other features and advantages of the present invention will become more apparent by describing in detailed exemplary embodiments thereof with reference to the accompanying drawings, in which.

DESCRIPTION OF THE EMBODIMENTS

Figure 1:
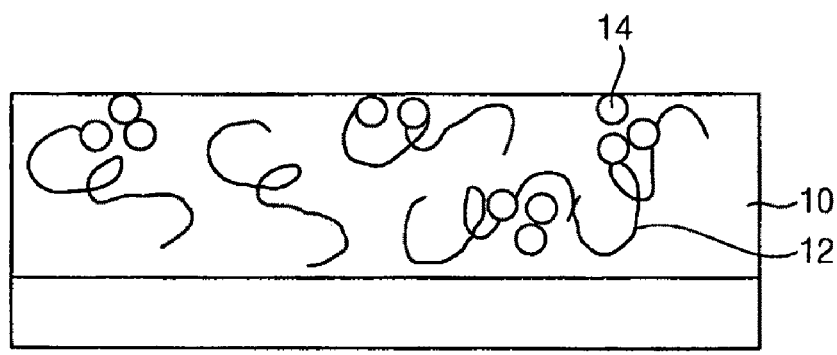
FIG. 1 is a cross-sectional view illustrating the distribution of a photoacid generator in a photoresist film formed from a conventional photoresist composition.

The present invention is described more fully hereinafter with reference to the accompanying drawings, in which exemplary embodiments of the present invention are shown. The present invention may, however, be embodied in many different forms and should not be construed as limited to the exemplary embodiments set forth herein. Rather, these embodiments are provided so that this disclosure will be thorough and complete, and help convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be on, connected to, or coupled to the other element or layer, directly or not directly (wherein intervening elements or layers may be present). In contrast, when an element is referred to as being "directly on," "directly connected to" or "directly coupled to" another element or layer, there are no intervening elements or layers present. Like reference numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (e.g., rotated 90 degrees or at other orientations) and the spatially relative descriptors used herein interpreted accordingly.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments of the present invention are described herein with reference to cross-section illustrations that are schematic illustrations of idealized embodiments (and intermediate structures) of the present invention. As such, variations from the shapes of the illustrations accordingly, for example, due to manufacturing techniques and/or tolerances, are to be expected. Thus, exemplary embodiments of the present invention should not be construed as limited to the particular shapes of regions illustrated herein but are to include deviations in shapes that result, for example, from manufacturing. For example, an implanted region illustrated as a rectangle can have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Photoacid Generator

A photoacid generator according to exemplary embodiments of the present invention has hydrophilic characteristics. The photoacid generator includes a sulfonium-salt cationic group and a sulfonium-salt anionic group having a hydrophilic site. For example, the sulfonium-salt cationic group may be represented by the following Chemical Formulas 1, 2, 3 and 4.

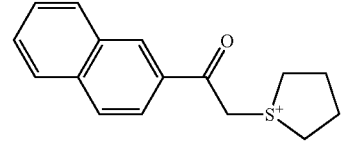

<Chemical Formula 1>

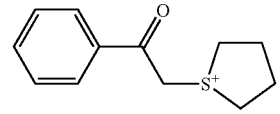

<Chemical Formula 2>

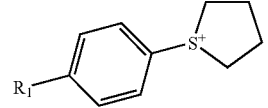

<Chemical Formula 3>

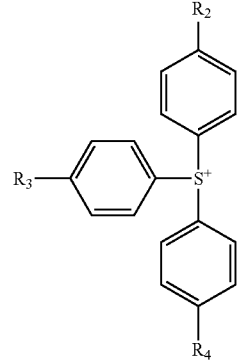

<Chemical Formula 4>

In Chemical Formula 3, $R_1$ represents a hydrogen atom or an alkyl group having 1 to 5 carbon atoms. An example of the sulfonium-salt cationic group represented by Chemical Formula 1 is monophenyl sulfonium. In Chemical Formula 4, $R_2$, $R_3$ and $R_4$ independently represent a hydrogen atom or an alkyl group having 1 to 5 carbon atoms. An example of the sulfonium-salt cationic group represented by Chemical Formula 4 is triphenyl sulfonium.

The sulfonium-salt anionic group may be represented by the following Chemical Formula 5.

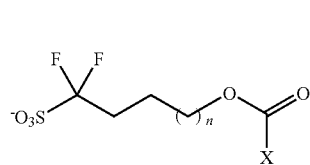

<Chemical Formula 5>

In Chemical Formula 5, n presents a natural number of 1 to 3, and X represents a cyclic group having 4 to 10 carbon atoms, an alkyl group having 1 to 10 carbon atoms, a cycloalkyl group having 4 to 10 carbon atoms, an adamantyl group, a cycloheptyl group containing an oxygen atom, etc. For example, when X of Chemical Formula 5 is an adamantyl group, the sulfonium-salt anionic group may be represented by the following Chemical Formula 5-1. In Chemical Formula 5-1, n represents a natural number of 1 to 3.

<Chemical Formula 5-1>

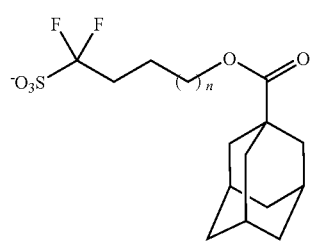

As another example, when X of Chemical Formula 5 is a cycloheptyl group containing an oxygen atom, the sulfonium-salt anionic group may be represented by the following Chemical Formula 5-2. In Chemical Formula 5-2, n represents a natural number of 1 to 3. Particularly, examples of the cycloheptyl group containing an oxygen atom may include 4,7,7-trimethyl-2-oxabicyclo[2.2.1]heptane.

<Chemical Formula 5-2>

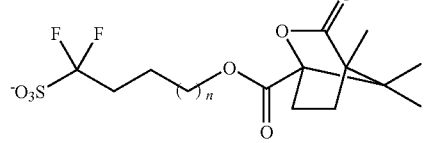

When the photoacid generator according to exemplary embodiments of the present invention includes the sulfonium-salt anionic group represented by Chemical Formula 5-1 and the sulfonium-salt cationic group represented by Chemical Formula 1, the photoacid generator may be represented by the following Chemical Formula 1-1. In Chemical Formula 1-1, n represents a natural number of 1 to 3 and may be preferably 1.

<Chemical Formula 1-1>

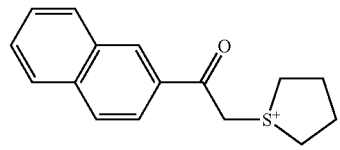

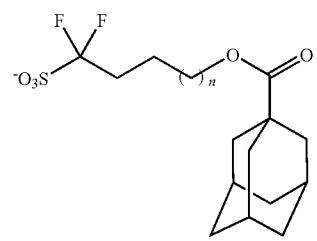

When the photoacid generator according to exemplary embodiments of the present invention includes the sulfonium-salt anionic group represented by Chemical Formula 5-2 and the sulfonium-salt cationic group represented by Chemical Formula 1, the photoacid generator may be represented by the following Chemical Formula 1-2. In Chemical Formula 1-2, n represents a natural number of 1 to 3, e.g., 1.

<Chemical Formula 1-2>

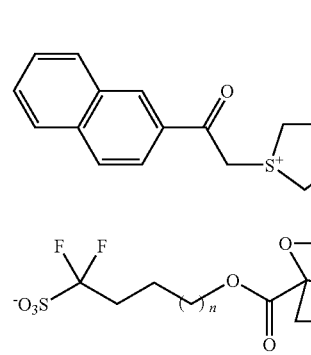

When the photoacid generator according to exemplary embodiments of the present invention includes the sulfonium-salt anionic group represented by Chemical Formula 5-1 and the sulfonium-salt cationic group represented by Chemical Formula 2, the photoacid generator may be represented by the following Chemical Formula 2-1. In Chemical Formula 2-1, n represents a natural number of 1 to 3, e.g., 1.

<Chemical Formula 2-1>

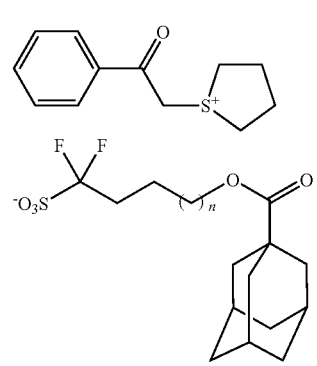

When the photoacid generator according to exemplary embodiments of the present invention includes the sulfonium-salt anionic group represented by Chemical Formula 5-2 and the sulfonium-salt cationic group represented by Chemical Formula 2, the photoacid generator may be represented by the following Chemical Formula 2-2. In Chemical Formula 2-2, n represents a natural number of 1 to 3, e.g., 1.

<Chemical Formula 2-2>

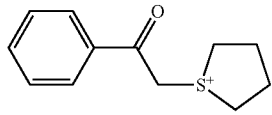

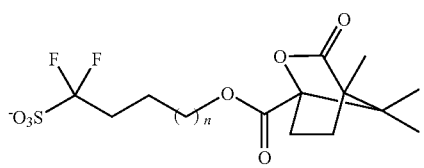

When the photoacid generator according to exemplary embodiments of the present invention includes the sulfonium-salt anionic group represented by Chemical Formula 5-1 and the sulfonium-salt cationic group represented by Chemical Formula 3, the photoacid generator may be represented by the following Chemical Formula 3-1. In Chemical Formula 3-1, n represents a natural number of 1 to 3, and $R_1$ represents an alkyl group having 1 to 3 carbon atoms. n may represent 1, and $R_1$ may represent methyl group.

<Chemical Formula 3-1>

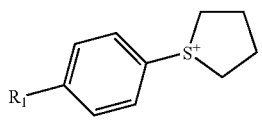

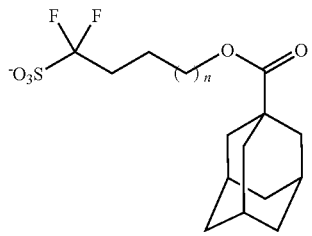

When the photoacid generator according to exemplary embodiments of the present invention includes the sulfonium-salt anionic group represented by Chemical Formula 5-2 and the sulfonium-salt cationic group represented by Chemical Formula 3, the photoacid generator may be represented by the following Chemical Formula 3-2. In Chemical Formula 3-2, n represents a natural number of 1 to 3, and $R_1$ represents an alkyl group having 1 to 3 carbon atoms. n may represent 1.

<Chemical Formula 3-2>

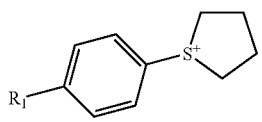

-continued

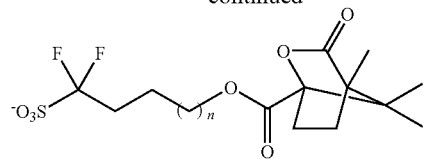

When the photoacid generator according to exemplary embodiments of the present invention includes the sulfonium-salt anionic group represented by Chemical Formula 5-1 and the sulfonium-salt cationic group represented by Chemical Formula 4, the photoacid generator may be represented by the following Chemical Formula 4-1. In Chemical Formula 4-1, n represents a natural number of 1 to 3, and $R_2$, $R_3$ and $R_4$ independently represent a hydrogen atom or an alkyl group having 1 to 5 carbon atoms. n may represent 1.

<Chemical Formula 4-1>

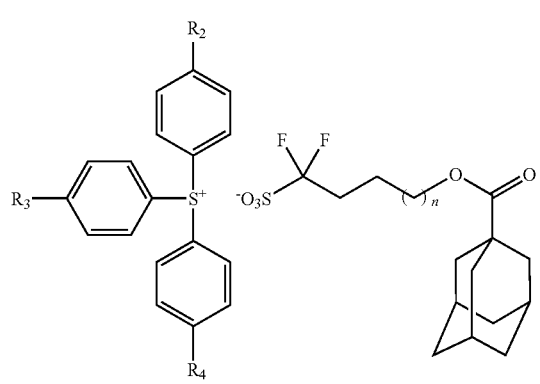

When the photoacid generator according to exemplary embodiments of the present invention includes the sulfonium-salt anionic group represented by Chemical Formula 5-2 and the sulfonium-salt cationic group represented by Chemical Formula 4, the photoacid generator may be represented by the following Chemical Formula 4-2. In Chemical Formula 4-2, n represents a natural number of 1 to 3, and $R_2$, $R_3$ and $R_4$ independently represents a hydrogen atom or an alkyl group having 1 to 5 carbon atoms. n may represent 1.

<Chemical Formula 4-2>

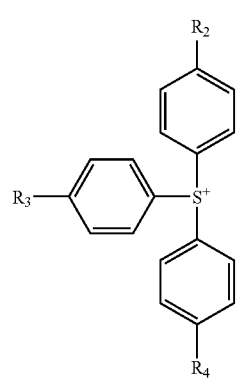

-continued

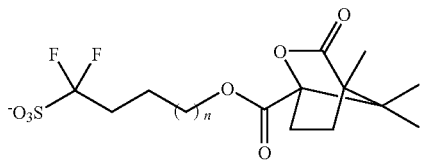

The photoacid generator that may be represented by Chemical Formulas 1-1 through 4-2 may be reacted with light to generate a sulfonic acid represented by the following Chemical Formula 6.

<Chemical Formula 6>

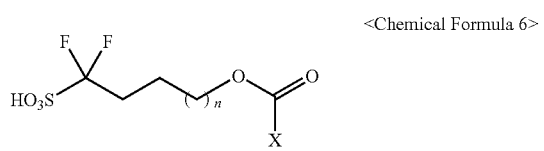

In Chemical Formula 6, n represents a natural number of 1 to 3, and X may represent a cyclic group having 4 to 10 carbon atoms, an adamantyl group, a cycloheptyl group containing an oxygen atom, etc.

For example, when X of Chemical Formula 6 represents an adamantyl group, the sulfonic acid may be represented by the following Chemical Formula 6-1. In Chemical Formula 6-1, n represents 1 to 3.

<Chemical Formula 6-1>

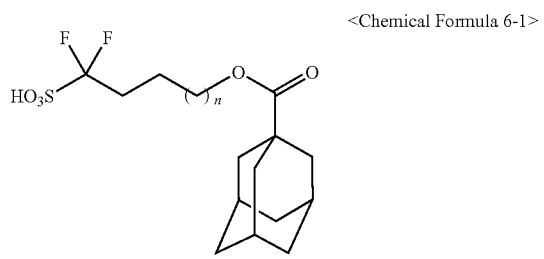

For example, when X of Chemical Formula 6 represents a cycloheptyl group containing an oxygen atom, the sulfonic acid may be represented by the following Chemical Formula 6-2. In Chemical Formula 6-2, n represents 1 to 3. An example of the cycloheptyl group containing an oxygen atom is 4,7,7-trimethyl-2-oxabicyclo[2.2.1]heptane.

<Chemical Formula 6-2>

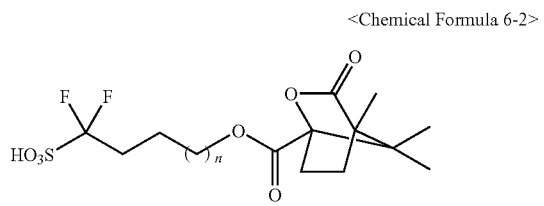

The photoacid generator contains fluorine having hydrophobic characteristics. However, the content of the fluorine is small, and the photoacid generator further contains a carboxyl group having hydrophilic characteristics so that the photoacid generator has hydrophilic characteristics. Particularly, the photoacid generator according to exemplary embodiments of the present invention contains reduced fluorine content and increased carboxyl group content. Thus, the photoacid generator has hydrophilic characteristics. The photoacid generator having hydrophilic characteristics may be uniformly distributed in a resin having hydrophilic characteristics.

The photoacid generator including the monophenyl sulfonium-salt cationic group may have high transmittance compared to the photoacid generator including the triphenyl sulfonium-salt cationic group. Thus, the photoacid generator including the monophenyl sulfonium-salt cationic group may prevent and/or reduce deformation of a profile of a photoresist pattern. Furthermore, the photoacid generator including the monophenyl sulfonium-salt cationic group, in which a sulfur ion is substituted for a carbon atom of an alicyclic ring, may have a relatively high acid-generating ratio.

Photoresist Compositions Including a Photoacid Generator

Photoresist compositions according to exemplary embodiments of the present invention are coated on an object in order to form a photoresist pattern. The photoresist compositions include a resin being reacted with an acid, a solvent and a hydrophilic photoacid generator capable of reacting with light to generate the acid.

The resin in the photoresist compositions is decomposed in the presence of an acid so that solubility of the resin is increased in a developing solution. A main chain and/or a branch chain of the resin have an acid-decomposing group (hereinafter referred to as a blocking group) that may be decomposed by an acid.

The blocking group is separated from the main chain of the resin by reaction with an acid, and a hydrogen atom of a carboxyl group or a hydroxyl group is substituted. The blocking group may have a lactone structure, an adamantyl structure, a cyclic structure, etc.

In some embodiments, the resin in the photoresist composition includes a methacrylate repeat unit having a blocking group. For example, the resin may include a methacrylate repeat unit having the blocking group having the lactone structure, a methacrylate repeat unit having the blocking group having the adamantyl structure, etc.

For example, the methacrylate repeat unit having the blocking group having the lactone structure may be represented by the following chemical formulas. In the chemical formulas, $R_x$ represents a hydrogen atom or methyl group.

(IV-1)

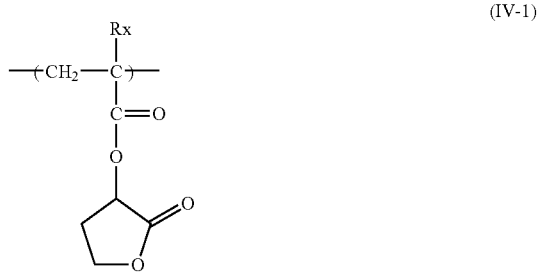

-continued
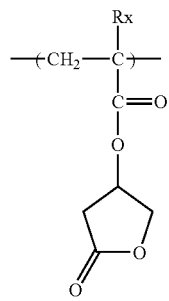 (IV-2)
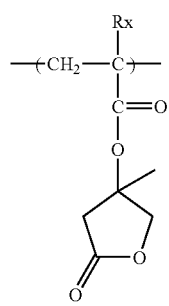 (IV-3)
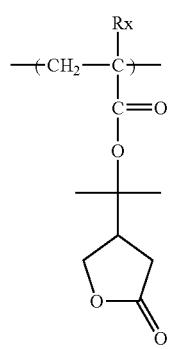 (IV-4)
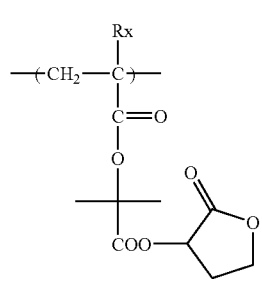 (IV-5)
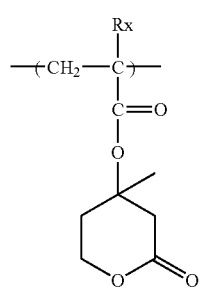 (IV-6)
-continued
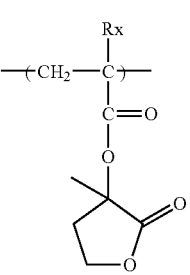 (IV-7)
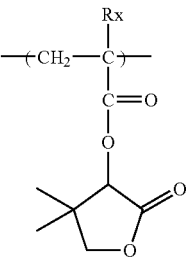 (IV-8)
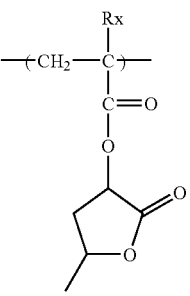 (IV-9)
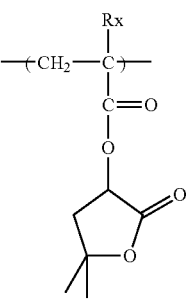 (IV-10)
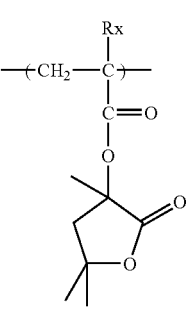 (IV-11)

-continued

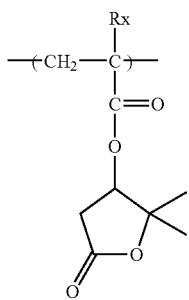
(IV-12)

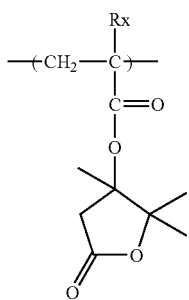
(IV-13)

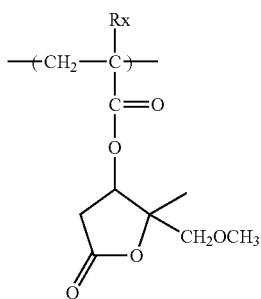
(IV-14)

For example, the methacrylate repeat unit having the blocking group having the adamantyl structure may be represented by the following Chemical Formula V.

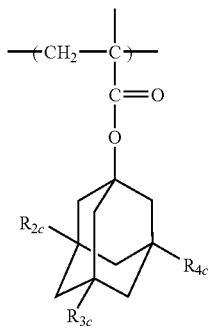
<Chemical Formula V>

In Chemical Formula V, $R_{2c}$, $R_{3c}$ and $R_{4c}$ independently represent a hydrogen atom or hydroxyl group.

The resin in the photoresist composition may include a first methacrylate repeat unit having a blocking group of a first adamantyl structure, a second methacrylate repeat unit having a blocking group of a lactone structure and a third methacrylate repeat unit having a blocking group of a second adamantyl structure. The blocking group of the first adamantyl structure has a molecular weight greater than a molecular weight of the blocking group of the second adamantyl structure.

When the content of the resin in the photoresist composition is less than 4% by weight based on a total weight of the photoresist composition, a photoresist pattern used for etching an object layer is not well formed. When the content of the resin in the photoresist composition is more than 10% by weight, a photoresist pattern may not have a uniform thickness.

The photoacid generator in the photoresist composition is reacted with light to generate a sulfonic acid represented by the following Chemical Formula 6. The photoacid generator includes a sulfonium-salt cationic group represented by one of the following Chemical Formulas 1, 2, 3 and 4 and a sulfonium-salt anionic group having a hydrophilic site and being represented by the following Chemical Formula 5. Thus, the photoacid generator has hydrophilic characteristics.

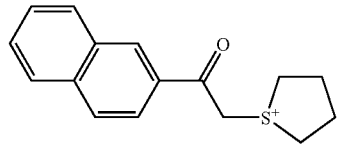
<Chemical Formula 1>

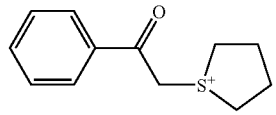
<Chemical Formula 2>

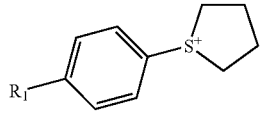
<Chemical Formula 3>

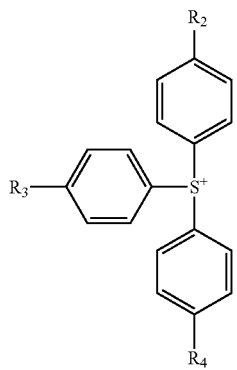
<Chemical Formula 4>

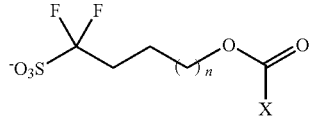
<Chemical Formula 5>

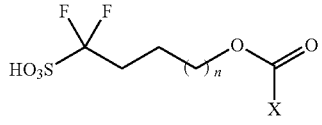
<Chemical Formula 6>

In Chemical Formula 3, $R_1$ represents a hydrogen atom or an alkyl group having 1 to 5 carbon atoms. An example of the sulfonium-salt anionic group represented by Chemical Formula 3 is monophenyl sulfonium. In Chemical Formula 4, $R_2$, $R_3$ and $R_4$ independently represent a hydrogen atom or an alkyl group having 1 to 5 carbon atoms. An example of the sulfonium-salt cationic group represented by Chemical Formula 4 is triphenyl sulfonium.

In Chemical Formula 5, n represents a natural number of 1 to 3, and X represents a cyclic group having 4 to 10 carbon atoms, an alkyl group having 1 to 10 carbon atoms, a cycloalkyl group having 4 to 10 carbon atoms, an adamantyl group, a cycloheptyl group containing an oxygen atom, etc. In exemplary embodiments, X represents an adamantyl group or a cycloheptyl group containing an oxygen atom. The photoacid generator according to exemplary embodiments of the present invention may include the sulfonium-salt anionic group represented by Chemical Formula 5. For example, the photoacid generator may be represented by the above-explained Chemical Formulas 1-1, 1-2, 2-1, 2-2, 3-1, 3-2, 4-1, 4-2, etc. The photoacid generator may be reacted with light to generate the acid represented by Chemical Formula 6.

The photoacid generator has hydrophilic characteristics. Thus, the photoacid generator may be easily mixed with the resin in the photoresist composition. The photoacid generator may be uniformly distributed in a photoresist film formed from the photoresist composition. The photoacid generator is fully described in the above. Thus, any further explanations in these regards will be omitted.

When the content of the photoacid generator is less than about 0.1% by weight based on a total weight of the photoresist composition, the amount of acid generated in an exposing process is not sufficient. The ability to separate the blocking group from the resin may be reduced. When the content of the photoacid generator is more than about 0.5% by weight, the amount of acid generated in an exposing process is excessive. Thus, top loss of a photoresist pattern may be increased. Therefore, the photoresist composition may include about 0.1% to about 0.5% by weight of the photoacid generator, e.g., about 0.15% to about 0.4% by weight of the photoacid generator.

Examples of the solvent include ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methyl ether acetate, propylene glycol propyl ether acetate, diethylene glycol dimethyl ether, ethyl lactate, toluene, xylene, methyl ethyl ketone, cyclohexanone, 2-heptanone, 3-heptanone, 4-heptanone, etc. These can be used alone or in a combination thereof. The solvent may be changed depending on components of the photoresist composition. Thus, examples of the solvent are not limited.

The photoresist composition may further include an additive to improve certain characteristics. Examples of additives include an organic base, a surfactant, etc. The organic base may prevent and/or reduce the effect of a basic compound, for example, amine, in an atmosphere after the photoresist pattern is exposed to light. Furthermore, the organic base may control the shape of the photoresist pattern. Examples of organic bases include trimethylamine, triisobutylamine, triisooctylamine, triisodecylamine, diethanolamine, triethanolamine, etc. The surfactant may improve coating ability of the photoresist composition, and may prevent stripes from appearing on a surface of a photoresist film formed from the photoresist composition. Examples of surfactants include Surflon SC-103 and SR-100 (manufactured by Asahi Glass Co., Ltd. in Japan), EF-361 (manufactured by Tohoku Hiryo Co., Ltd. in Japan), and Fluorad Fc-431, Fc-135, Fc-98, Fc-430 and Fc-176 (manufactured by Sumitomo 3M Ltd. in Japan), etc. The additives can be used alone or in a combination thereof.

The photoacid generators have hydrophilic characteristics so that the photoacid generators may be uniformly distributed in resins having hydrophilic characteristics. Thus, the photoresist compositions including the photoacid generators may form photoresist patterns having uniform profiles. The photoresist compositions including the photoacid generators containing a monophenyl group have relatively high transmittance to prevent and/or to reduce deformation of the profiles of photoresist patterns.

Methods of Forming a Pattern

FIGS. 2, 3, 4 and 5 are cross-sectional views illustrating a method of forming pattern according to exemplary embodiments of the present invention.

Figure 2:
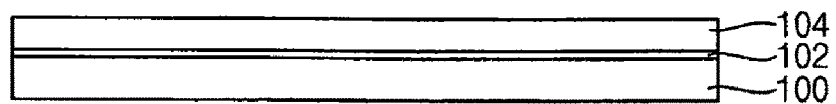
FIGS. 2, 3, 4 and 5 are cross-sectional views illustrating a method of forming a pattern according to an exemplary embodiment of the present invention.

Referring to FIG. 2, an object for etching is prepared. An example of the object is a semiconductor substrate 100 and a thin-film layer 102 formed on the semiconductor substrate 100. Hereinafter, etching the thin-film layer 102 as an example will be explained. Examples of a material that may be used for the thin-film layer 102 include silicon nitride, polysilicon, silicon oxide, etc.

After the thin-film layer 102 is cleaned in order to remove impurities remaining on a surface of the thin-film layer 102, a photoresist composition is coated on the thin-film layer 102 to form a photoresist film 104. The photoresist composition includes a methacrylate resin, a photoacid generator having a hydrophilic site and an organic solvent.

The photoacid generator of the photoresist composition is reacted with light to generate a sulfonic acid represented by the following Chemical Formula 6. The photoacid generator includes a sulfonium-salt cationic group represented by one of the following Chemical Formulas 1, 2, 3 and 4 and a sulfonium-salt anionic group having a hydrophilic site and represented by the following Chemical Formula 5. Thus, the photoacid generator has hydrophilic characteristics.

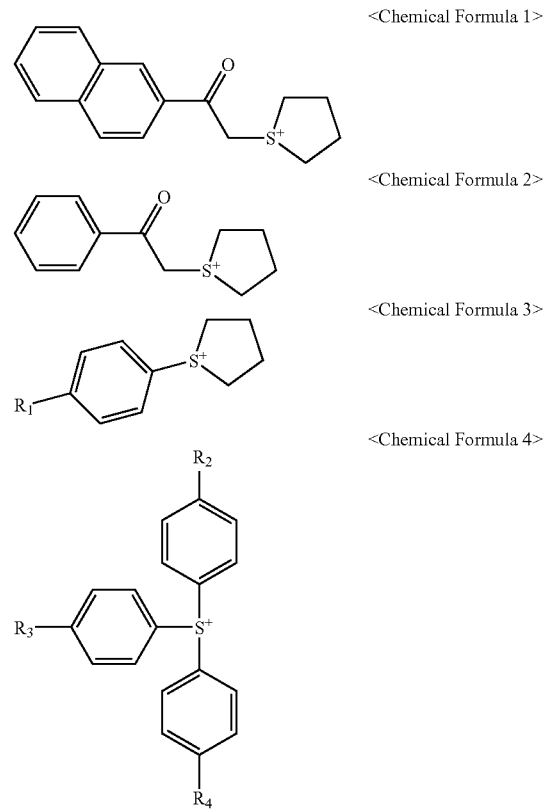

<Chemical Formula 1>

<Chemical Formula 2>

<Chemical Formula 3>

<Chemical Formula 4>

-continued

<Chemical Formula 5>

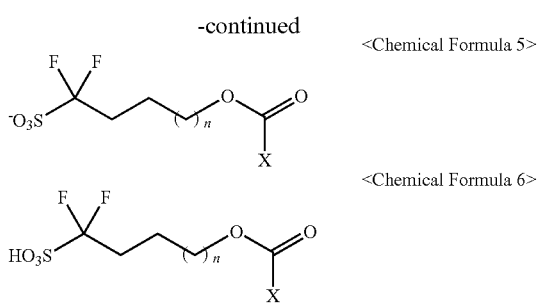

<Chemical Formula 6>

In Chemical Formula 3, $R_1$ represents a hydrogen atom or an alkyl group having 1 to 5 carbon atoms. An example of the sulfonium-salt cationic group represented by Chemical Formula 3 is monophenyl sulfonium. In Chemical Formula 4, $R_2$ $R_3$ and $R_4$ independently represent a hydrogen atom or an alkyl group having 1 to 5 carbon atoms. An example of the sulfonium-salt cationic group represented by Chemical Formula 4 is triphenyl sulfonium.

In Chemical Formula 5, n presents a natural number of 1 to 3, and X represents a cyclic group having 4 to 10 carbon atoms, an alkyl group having 1 to 10 carbon atoms, a cycloalkyl group having 4 to 10 carbon atoms, an adamantyl group, a cycloheptyl group containing an oxygen atom, etc.

For example, examples of the photoacid generator may be represented by above-explained Chemical Formulas 1-1, 1-2, 2-1, 2-2, 3-1, 3-2, 4-1, 4-2, etc. The photoacid generator may be reacted with light to generate the acid represented by Chemical Formula 6. The photoacid generator is fully described in the above. Thus, any further explanations in these regards will be omitted.

A first baking process is performed to heat the substrate 100 having the photoresist film 104. The first baking process may be performed at a temperature of about 90° C. to about 120° C. Accordingly, the adhesion of the photoresist film 104 with respect to the thin-film layer 102 may be increased.

Figure 3:
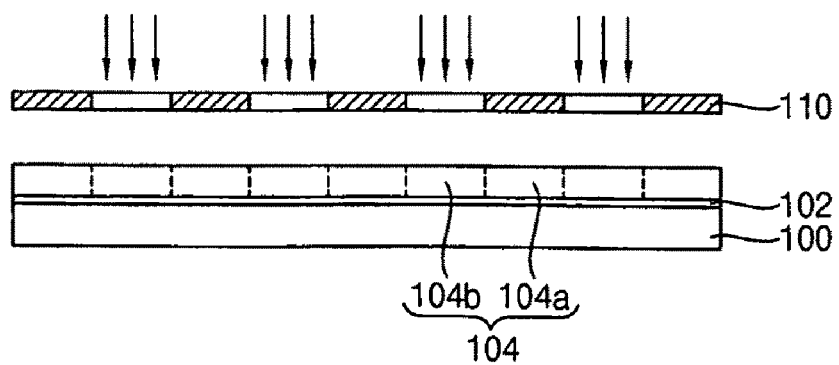

Referring to FIG. 3, the photoresist film 104 is selectively exposed to light. For example, a mask having a circuit pattern is disposed on a mask stage of an exposing device. The mask is aligned on the photoresist film 104. Thereafter, the mask 110 is exposed to light for a predetermined time period so that a predetermined region of the photoresist film 104 formed on the substrate 100 is selectively reacted with the light passing through the mask 110.

Examples of the light that may be used for the exposing process include an argon fluoride (ArF) laser having a wavelength of about 193 nm, a krypton fluoride (KrF) laser having a wavelength of about 248 nm, a fluorine (F2) laser, a mercury xenon (Hg—Xe) laser, etc. An exposed portion 104b of the photoresist film has relatively high hydrophilic characteristics compared to an unexposed portion 104a of the photoresist film. Thus, the exposed portion 104b of the photoresist film has solubility different from that of the unexposed portion 104a of the photoresist film.

Thereafter, a second baking process is performed on the substrate 100. The second baking process may be performed at a temperature of about 90° C. to about 150° C. The exposed portion 104b of the photoresist film may then be easily dissolved in a developing solution.

Figure 4:

Referring to FIG. 4, a developing solution is contacted to the exposed portion 104b of the photoresist film to dissolve the exposed portion 104b of the photoresist film so that the exposed portion 104b of the photoresist film may be removed. Thus, a photoresist pattern 106 may be formed. For example, tetramethyl ammonium hydroxide (TMAH) may be used as the developing solution to remove the exposed portion 104b of the photoresist film. The exposed portion 104b of the photoresist film and the unexposed portion 104a of the photoresist film have different hydrophilic characteristics so that the exposed portion 104b of the photoresist film is selectively removed by the developing solution. Thereafter, a cleaning process, a drying process, etc. are performed to form the photoresist pattern 106.

The photoresist pattern 106 may have a uniform profile since the photoacid generator is distributed in the photoresist film 104 to reduce (e.g., minimize) a diffusion path of an acid. Furthermore, the-photoresist pattern may have a desired diameter or a desired distance.

Figure 5:
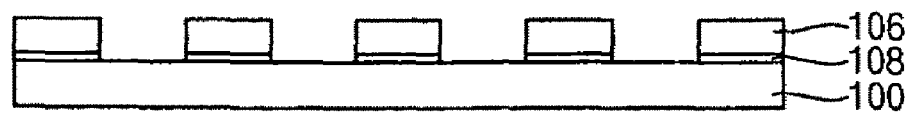

Referring to FIG. 5, the thin-film layer exposed through the photoresist pattern 106 is etched using the photoresist pattern 106 as an etching mask. Thus, a thin-film pattern 108 having a desired size and a uniform profile may be formed.

Hereinafter, the embodiments of the present invention are described more fully with reference to synthetic examples of a photoacid generator, preparation examples and evaluations of a photoresist composition including the photoacid generator. However, it is understood that the present invention should not be limited to these examples but various changes and modifications can be made by one of ordinary skill in the art within the spirit and scope of the present invention.

SYNTHETIC EXAMPLE 1

4-bromo-4,4-difluorobutanol was reacted with adamantane carbonyl chloride in a molar ratio of about 1:1. The reaction was carried out in ethyl ether at about 0° C. under a nitrogen atmosphere. The reaction mixture was allowed to warm to a room temperature, and then stirred for about 6 hours. The obtained product was sulfonated using sulfuric acid to prepare a first sulfonic acid represented by the following Chemical Formula A. In Chemical Formula A, n represents 1.

<Chemical Formula A>

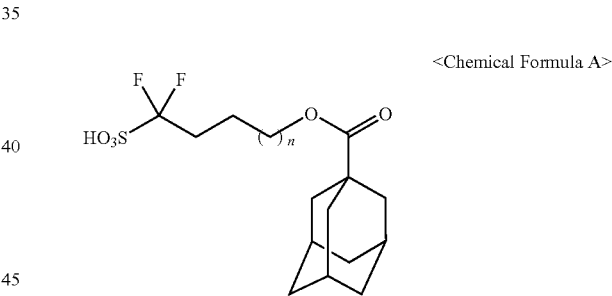

SYNTHETIC EXAMPLE 2

4-bromo-4,4-difluorobutanol was reacted with 4,7,7-trimethyl-3-oxo-2-oxa-bicyclo[2.2.1]heptane-1-carbonyl chloride in a molar ratio of about 1:1. The reaction conditions were substantially the same as those of Synthetic Example 1. The obtained product was sulfonated using sulfuric acid to prepare a second sulfonic acid represented by the following Chemical Formula B. In Chemical Formula B, n represents 1.

<Chemical Formula B>

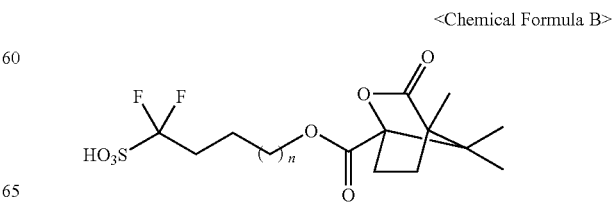

EXAMPLE 1

The first sulfonic acid of Synthetic Example 1 was reacted with a first monophenyl sulfonium chloride to prepare a photoacid generator represented by the following Chemical Formula 1-1. In Chemical Formula 1-1, n represents 1. Particularly, naphthalenylcarbonylethyl tetramethylenesulfonium chloride was reacted with the first sulfonic acid represented by Chemical Formula A in a molar ratio of about 1:1. The reaction was carried out in ethyl ether at about 0° C. under a nitrogen atmosphere. The reaction mixture was allowed to warm to a room temperature, and then stirred for about 6 hours.

<Chemical Formula 1-1>

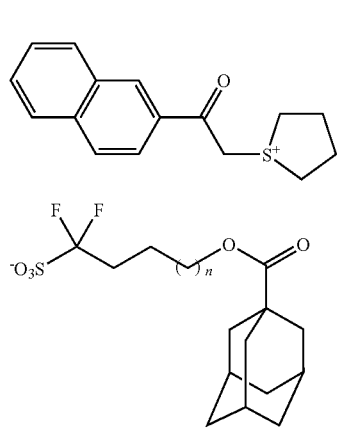

The chemical structure of the photoacid generator was confirmed using a $^1$H-NMR (Nuclear Magnetic Resonance), a mass spectroscopy and an infrared (IR) spectroscopy. The $^1$H-NMR spectrum showed chemical shifts at 8.29 ppm (C—H in naphthalene ring), 7.74 ppm (C—H in naphthalene ring), 4.07 ppm ($CH_2CH_2CH_2O$), 2.56 ppm ($COCH_2S$), 2.30 ppm ($SCH_2CH_2CH_2CH_2$), 2.17 ppm ($CF_2CH_2CH_2CH_2OCO$), 1.6 ppm ($CH_2CH$ in adamantane), and 1.2 ppm ($CH_2CHCH_2$ in adamantane) relative to tetramethylsilane. The mass spectrum showed peaks at 257.10 of the monophenylsulfonium cation and 351.78 of the sulfonate anion. The IR spectrum showed a peak at 1725 (C=O, ester).

EXAMPLE 2

The second sulfonic acid of Synthetic Example 2 was reacted with a first monophenyl sulfonium chloride in the conditions substantially the same as those of Example 1 to prepare a photoacid generator represented by the following Chemical Formula 1-2. In Chemical Formula 1-2, n represents 1.

<Chemical Formula 1-2>

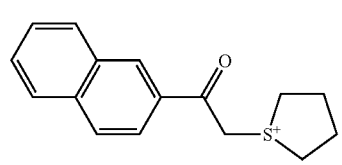

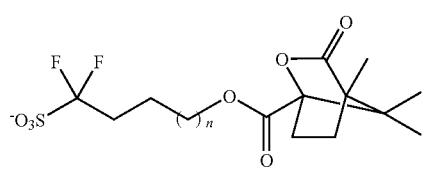

The chemical structure of the photoacid generator was confirmed using 1H-NMR, a mass spectroscopy and an IR spectroscopy. The $^1$H-NMR spectrum showed chemical shifts at 8.29 ppm (C—H in naphthalene ring), 7.74 ppm (C—H in naphthalene ring), 4.07 ppm ($CH_2CH_2CH_2O$), 2.56 ppm ($COCH_2S$), 2.30 ppm ($SCH_2CH_2CH_2CH_2$), 2.17 ppm ($CF_2CH_2CH_2CH_2OCO$), 1.95 ppm ($CH_2$ in bicyclic ester), and 1.1 ppm ($CH_3$) relative to tetramethylsilane. The mass spectrum showed peaks at 257.10 of the monophenylsulfonium cation and 383.10 of the sulfonate anion. The IR spectrum showed a peak at 1784 (C=O, ester).

EXAMPLE 3

The first sulfonic acid of Synthetic Example 1 was reacted with a second monophenyl sulfonium chloride to prepare a photoacid generator represented by the following Chemical Formula 2-1. In Chemical Formula 2-1, n represents 1. Particularly, phenylcarbonylethyl tetramethylenesulfonium chloride was reacted with the first sulfonic acid represented by Chemical Formula A in a molar ratio of about 1:1. The reaction was carried out in ethyl ether at about 0° C. under a nitrogen atmosphere. The reaction mixture was allowed to warm to a room temperature, and then stirred for about 6 hours.

<Chemical Formula 2-1>

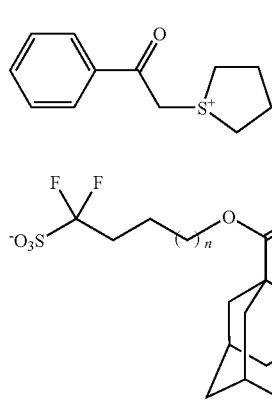

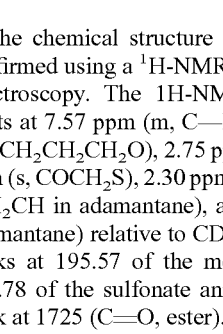

The chemical structure of the photoacid generator was confirmed using a $^1$H-NMR, a mass spectroscopy and an IR spectroscopy. The 1H-NMR spectrum showed chemical shifts at 7.57 ppm (m, C—H in benzene ring), 4.33 ppm (t, $CF_2CH_2CH_2CH_2O$), 2.75 ppm (m, $CH_2CH_2CH_2OCO$), 2.56 ppm (s, $COCH_2S$), 2.30 ppm ($SCH_2CH_2CH_2CH_2$), 1.79 ppm ($CH_2CH$ in adamantane), and 1.18 ppm (s, $CH_2CHCH_2$ in adamantane) relative to $CDCl_3$. The mass spectrum showed peaks at 195.57 of the monophenylsulfonium cation and 351.78 of the sulfonate anion. The IR spectrum showed a peak at 1725 (C=O, ester).

EXAMPLE 4

The second sulfonic acid of Synthetic Example 2 was reacted with a second monophenyl sulfonium chloride in the conditions substantially the same as those of Example 3 to prepare a photoacid generator represented by the following Chemical Formula 2-2. In Chemical Formula 2-2, n represents 1.

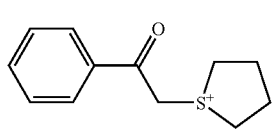

<Chemical Formula 2-2>

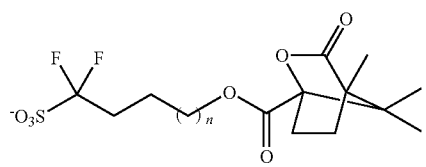

The chemical structure of the photoacid generator was confirmed using a 1H-NMR, a mass spectroscopy and an IR spectroscopy. The $^1$H-NMR spectrum showed chemical shifts at 7.57 ppm (m, C—H in benzene ring), 4.33 ppm (t, $CF_2CH_2CH_2CH_2O$), 2.75 ppm (m, $CH_2CH_2CH_2OCO$), 2.56 ppm (s, $COCH_2S$), 2.30 ppm ($SCH_2CH_2CH_2CH_2$), 1.9 ppm ($CH_2$ in bicyclic ester), and 1.1 ppm ($CH_3$) relative to $CDCl_3$. The mass spectrum showed peaks at 195.57 of the monophenylsulfonium cation and 383.10 of the sulfonate anion. The IR spectrum showed a peak at 1784 (C=O, ester).

EXAMPLE 5

The first sulfonic acid of Synthetic Example 1 was reacted with a third monophenyl sulfonium chloride to prepare a photoacid generator represented by the following Chemical Formula 3-1. In Chemical Formula 3-1, $R_1$ represents a methyl group, and n represents 1. Particularly, p-tolyl tetramethylenesulfonium chloride was reacted with the first sulfonic acid represented by Chemical Formula A in a molar ratio of about 1:1. The reaction was carried out in ethyl ether at about 0° C. under a nitrogen atmosphere. The reaction mixture was allowed to warm to a room temperature, and then stirred for about 6 hours.

<Chemical Formula 3-1>

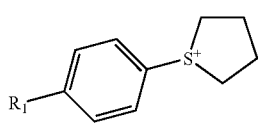

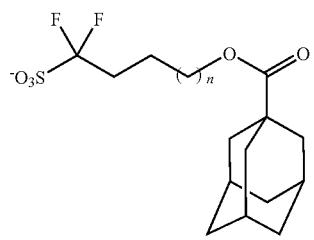

The chemical structure of the photoacid generator was confirmed using a $^1$H-NMR, a mass spectroscopy and an IR spectroscopy. The $^1$H-NMR spectrum showed chemical shifts at 7.1 ppm (C—H in benzene ring), 4.33 ppm ($CF_2CH_2CH_2CH_2O$), 2.75 ppm ($CH_2CH_2CH_2OCO$), 2.30 ppm ($SCH_2CH_2CH_2CH_2$), 1.79 ppm ($CH_2CH$ in adamantane), and 1.18 ppm ($CH_2CHCH_2$ in adamantane) relative to $CDCl_3$. The mass spectrum showed peaks at 179.09 of the monophenylsulfonium cation and 351.78 of the sulfonate anion. The IR spectrum showed a peak at 1725 (C=O, ester).

EXAMPLE 6

The second sulfonic acid of Synthetic Example 2 was reacted with a third monophenyl sulfonium chloride in the conditions substantially the same as those of Example 5 to prepare a photoacid generator represented by the following Chemical Formula 3-2. In Chemical Formula 3-2, $R_1$ represents a methyl group, and n represents 1.

<Chemical Formula 3-2>

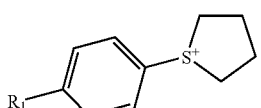

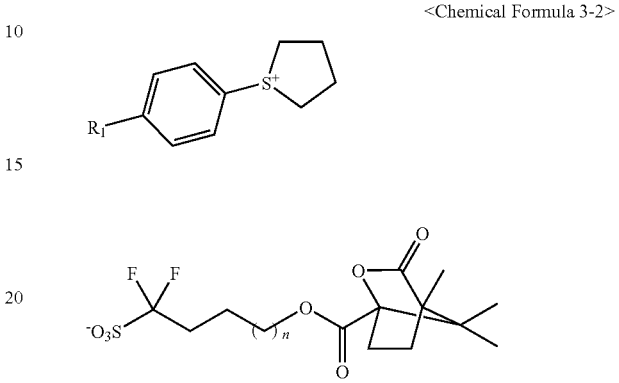

The chemical structure of the photoacid generator was confirmed using a $^1$H-NMR, a mass spectroscopy and an IR spectroscopy. The $^1$H-NMR spectrum showed chemical shifts at 7.1 ppm (C—H in benzene ring), 4.33 ppm ($CF_2CH_2CH_2CH_2O$), 2.75 ppm ($CH_2CH_2CH_2OCO$), 2.30 ppm ($SCH_2CH_2CH_2CH_2$) ppm ($CH_2$ in bicyclic ester), and 1.1 ppm ($CH_3$) relative to $CDCl_3$. The mass spectrum showed peaks at 179.05 of the monophenylsulfonium cation and 383.17 of the sulfonate anion. The IR spectrum showed a peak at 1784 (C=O, ester).

EXAMPLE 7

The first sulfonic acid of Synthetic Example 1 was reacted with triphenyl sulfonium chloride to prepare a photoacid generator represented by the following Chemical Formula 4-1. In Chemical Formula 4-1, each $R_2$, $R_3$ and $R_4$ represents a hydrogen atom, and n represents 1. Particularly, triphenylsulfonium chloride was reacted with the first sulfonic acid represented by Chemical Formula A in a molar ratio of about 1:1. The reaction was carried out in ethyl ether at about 0° C. under a nitrogen atmosphere. The reaction mixture was allowed to warm to a room temperature, and then stirred for about 6 hours.

<Chemical Formula 4-1>

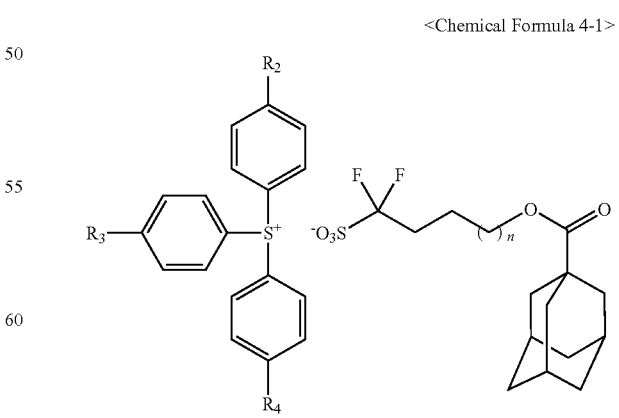

The chemical structure of the photoacid generator was confirmed using a $^1$H-NMR, a mass spectroscopy and an IR spectroscopy. The $^1$H-NMR spectrum showed chemical shifts at 7.57 ppm (C—H in benzene ring), 4.33 ppm (CF$_2$CH$_2$CH$_2$CH$_2$O), 2.75 ppm (CH$_2$CH$_2$CH$_2$OCO), 1.79 ppm (CH$_2$CH in adamantane), and 1.18 ppm (CH$_2$CHCH$_2$ in adamantane) relative to CDCl$_3$. The mass spectrum showed peaks at 263.31 of the triphenylsulfonium cation and 351.75 of the sulfonate anion. The IR spectrum showed a peak at 1725 (C=O, ester).

EXAMPLE 8

The second sulfonic acid of Synthetic Example 2 was reacted with triphenyl sulfonium chloride in the conditions substantially the same as those of Example 7 to prepare a photoacid generator represented by the following Chemical Formula 4-2. In Chemical Formula 4-2, each R$_2$, R$_3$ and R$_4$ represents a methyl group, and n represents 1.

<Chemical Formula 4-2>

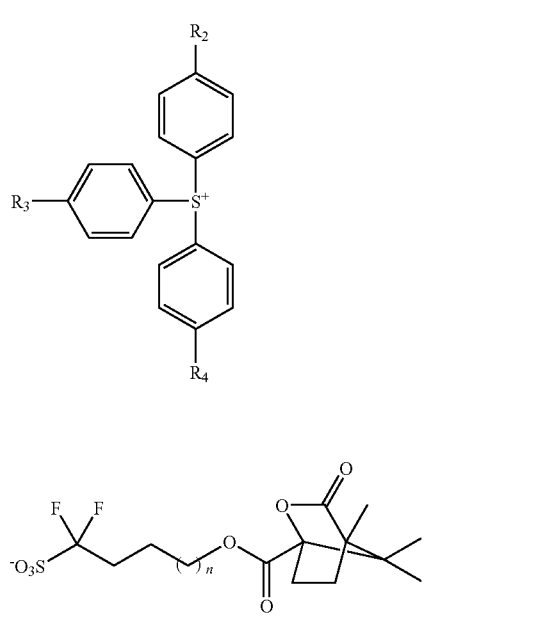

The chemical structure of the photoacid generator was confirmed using a $^1$H-NMR, a mass spectroscopy and an IR spectroscopy. The $^1$H-NMR spectrum showed chemical shifts at 7.73 ppm (C—H in benzene ring), 4.52 ppm (CF$_2$CH$_2$CH$_2$CH$_2$O), 2.82 ppm (CH$_2$CH$_2$CH$_2$OCO), 1.9 ppm (CH$_2$ in bicyclic ester), and 1.1 ppm (CH$_3$) relative to CDCl$_3$. The mass spectrum showed peaks at 263.38 of the triphenylsulfonium cation and 383.05 of the sulfonate anion. The IR spectrum showed a peak at 1780 (C=O, ester).

PREPARATION EXAMPLE 1

About 2 parts by weight of the photoacid generator of Synthetic Example 1 was dissolved in about 111 parts by weight of methacrylate resin and about 887 parts by weight of propylene glycol monomethyl ether acetate in a laboratory where far ultraviolet rays were blocked. Thereafter, the mixture was filtered through a membrane filter of about 0.2 μm to prepare a photoresist composition.

COMPARATIVE EXAMPLE

A photoresist composition was prepared through the same method as Preparation example 1 except that a photoacid generator represented by Chemical Formula 6 was used instead of the photoacid generator of Synthetic Example 1. In Chemical Formula 6, each R is a methyl group.

<Chemical Formula 6>

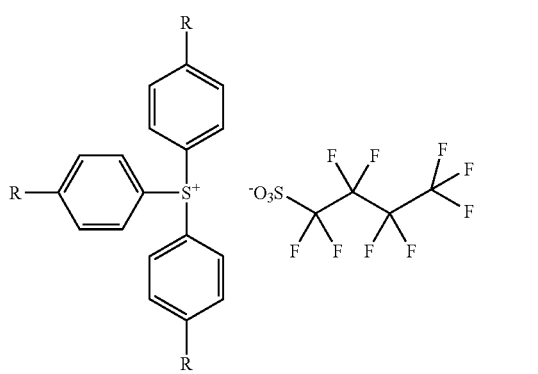

Evaluation of Photoresist Film

Each of the photoresist compositions of Preparation Example 1 and the Comparative Example was coated on a silicon substrate, and heated at a temperature of about 100° C. for about 90 seconds to form a photoresist film having a thickness of about 0.4 μm. Thereafter, a water droplet was dropped on the photoresist film, and the contact angle between the water droplet and the photoresist film was measured in order to evaluate the distribution of a photoacid generator in the photoresist film. When the contact angle between the water droplet and the photoresist film is measured, the distribution of a photoacid generator in the photoresist film may be indirectly known. The obtained results are shown in the following Table 1.

TABLE 1

|  | Preparation Example 1 | Comparative Example |
|---|---|---|
| Contact Angle (°) | 68 | 75 |

Referring to Table 1, the contact angle measured on the photoresist film formed from the photoresist composition of Preparation Example 1 was less than 70°. However, the contact angle measured on the photoresist film formed from the photoresist composition of the Comparative Example was about 75°.

Thus, it can be noted that the contact angle of a water droplet on a photoresist film may be different depending on a photoacid generator. As hydrophobic characteristics of a photoacid generator are increased, the photoacid generator may be distributed in an upper portion of a photoresist film so that the contact angle of a water droplet on a photoresist film is increased. Thus, a photoacid generator in the photoresist film may be more uniformly formed from the photoresist composition of Preparation Example 1.

Evaluation of Photoresist Pattern

Each of the photoresist compositions of Preparation Example 1 and the Comparative Example was coated on a silicon substrate, and heated at a temperature of about 100° C. for about 90 seconds to form a photoresist film having a thickness of about 0.4 μm. Thereafter, the photoresist film was selectively exposed to an Hg—Xe laser using a mask, and then heated at a temperature of about 110° C. for about 90 seconds. Thereafter, an exposed portion of the photoresist film was removed using a developing solution including about 2.38% by weight of tetramethyl ammonium hydroxide (TMAH). Thereafter, a cleaning process to remove any remaining developing solution and a drying process were performed to form a photoresist pattern. The photoresist pattern was observed by an electron microscope so that scanning electron microscope (SEM) pictures shown in FIGS. 6 and 7 were obtained. The mask had a predetermined pattern such that the photoresist pattern was spaced apart from an adjacent photoresist pattern by about 100 nm in a y-coordinate direction.

Figure 6:
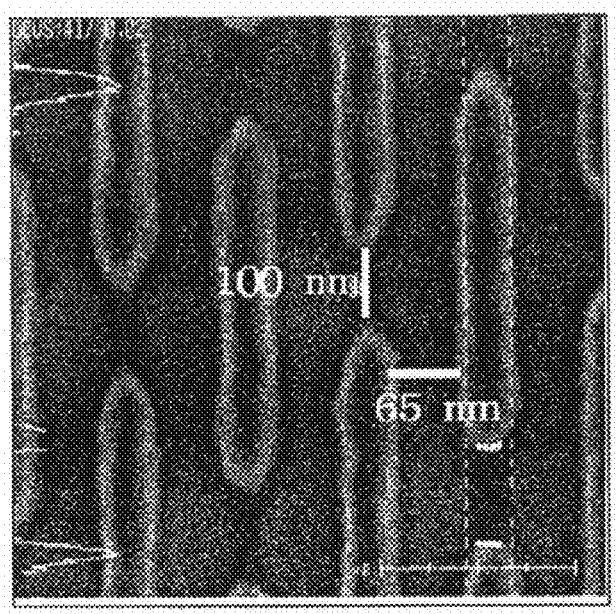
FIG. 6 is a scanning electron microscope (SEM) picture showing a photoresist pattern formed from a photoresist composition of Preparation Example 1.

FIG. 6 is an SEM picture showing a photoresist pattern formed from the photoresist composition of Preparation Example 1.

Referring to FIG. 6, the photoresist pattern formed from the photoresist composition of Preparation example 1 is spaced apart from an adjacent photoresist pattern by about 95 nm to about 100 nm in a y-coordinate direction. Thus, it can be noted that a ratio of a longitudinal length to a lateral length was improved. Furthermore, it can be noted that the photoresist pattern had a desirable profile, of which an upper portion was not damaged or round.

Figure 7:
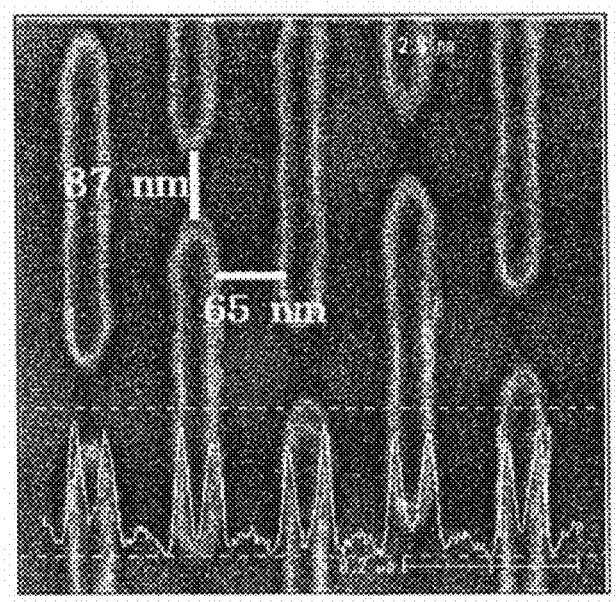
FIG. 7 is an SEM picture showing a photoresist pattern formed from a photoresist composition of Comparative Example.

FIG. 7 is an SEM picture showing a photoresist pattern formed from the photoresist composition of the Comparative Example.

Referring to FIG. 7, the photoresist pattern was intended to be spaced apart from an adjacent photoresist pattern by about 100 nm in a y-coordinate direction. However, the actual distance between the photoresist pattern and the adjacent photoresist pattern was about 87 nm. Thus, it can be noted that a ratio of a longitudinal length to a lateral length was not improved.

According to the above, a photoacid generator has hydrophilic characteristics similar to a resin of a photoresist composition so that the photoacid generator may be easily mixed with the resin. Thus, the photoacid generator may be uniformly distributed in a photoresist film. Accordingly, a diffusion length, by which an acid generated by the photoacid generator moves to a blocking group of the resin in the photoresist film, is short so that a photoresist pattern may have a uniform profile.

Furthermore, the photoresist composition including the photoacid generator may improve critical line width margins of iso-patterns formed with dense patterns, and may form a photoresist pattern, of which an upper portion is not damaged. Furthermore, the photoresist composition including the photoacid generator may form a photoresist film having high transmittance so that a photoresist pattern having a uniform profile may be formed.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of the present invention. Accordingly, all such modifications are intended to be included within the scope of the present invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The present invention is defined by the following claims, with equivalents of the claims to be included therein.

What is claimed is:

1. A photoacid generator having a sulfonium-salt cationic group selected from the group consisting of compounds represented by the following Chemical Formulas 1, 2, 3 and 4, and a sulfonium-salt anionic group represented by the following Chemical Formula 5 and containing a carboxyl group as a hydrophilic site, wherein $R_1$, $R_2$, $R_3$ and $R_4$ independently represent a hydrogen atom or an alkyl group having 1 to 5 carbon atoms, n represents a natural number of 1 to 3, and X represents one selected from the group consisting of a cyclic group having 4 to 10 carbon atoms, an adamantyl group and a cycloheptyl group containing an oxygen atom

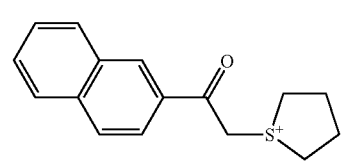
<Chemical Formula 1>

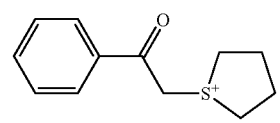
<Chemical Formula 2>

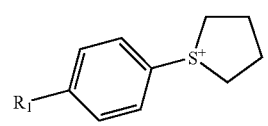
<Chemical Formula 3>

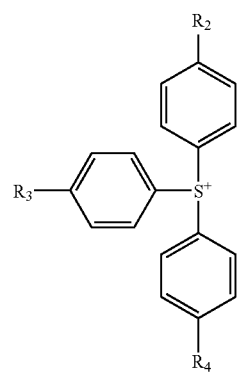
<Chemical Formula 4>

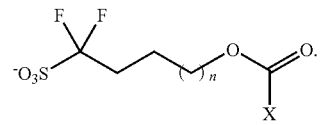
<Chemical Formula 5>

2. The photoacid generator of claim 1, wherein the photoacid generator is capable of reacting with light to form a sulfonic acid represented by the following Chemical Formula 6-1 or Chemical Formula 6-2, wherein n represents a natural number of 1 to 3

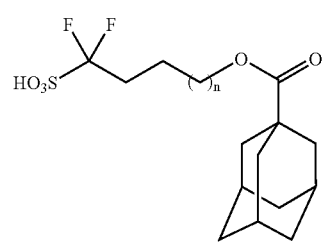
<Chemical Formula 6-1>

-continued

<Chemical Formula 6-2>

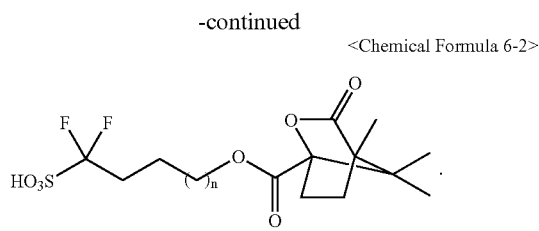

3. The photoacid generator of claim 1, wherein the photoacid generator is represented by the following Chemical Formula 1-1 or Chemical Formula 1-2, wherein n represents a natural number of 1 to 3

<Chemical Formula 1-1>

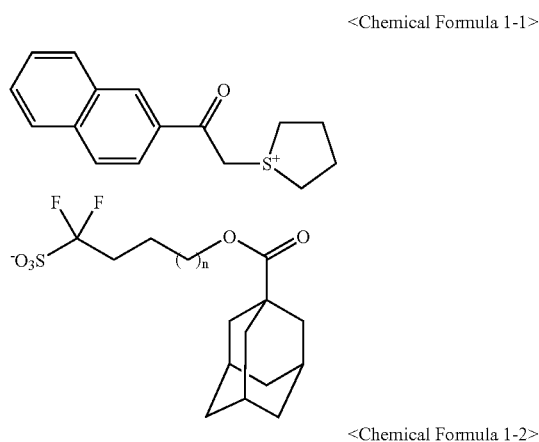

<Chemical Formula 1-2>

4. The photoacid generator of claim 1, wherein the photoacid generator is represented by the following Chemical Formula 2-1 or Chemical Formula 2-2, wherein n represents a natural number of 1 to 3

<Chemical Formula 2-1>

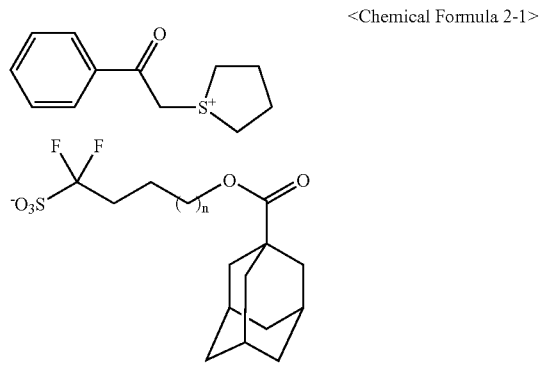

-continued

<Chemical Formula 2-2>

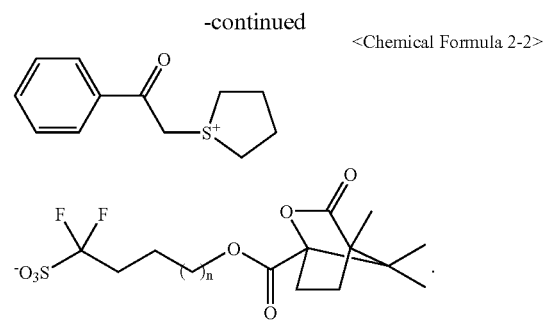

5. The photoacid generator of claim 1, wherein the photoacid generator is represented by the following Chemical Formula 3-1 or Chemical Formula 3-2, wherein n represents a natural number of 1 to 3, and $R_1$ represents a hydrogen atom or an alkyl group having 1 to 3 carbon atoms <Chemical Formula 3-1>

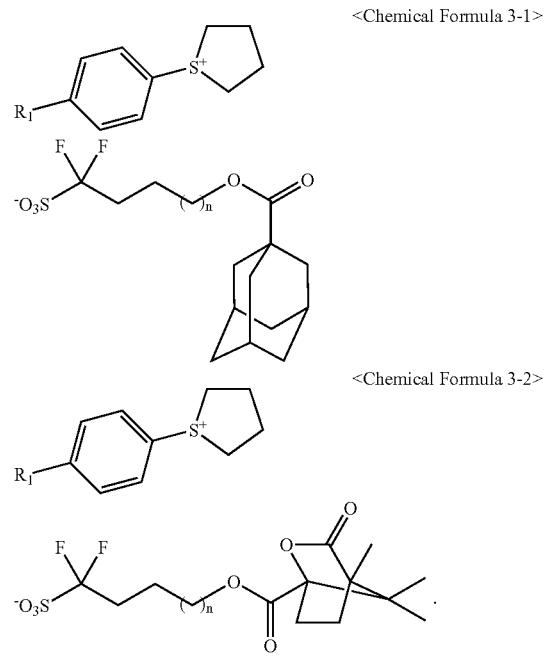

<Chemical Formula 3-2>

6. The photoacid generator of claim 1, wherein the photoacid generator is represented by the following Chemical Formula 4-1 or Chemical Formula 4-2, wherein n represents a natural number of 1 to 3, and $R_2$, $R_3$ and $R_4$ independently represent a hydrogen atom or an alkyl group having 1 to 5 carbon atoms <Chemical Formula 4-1>

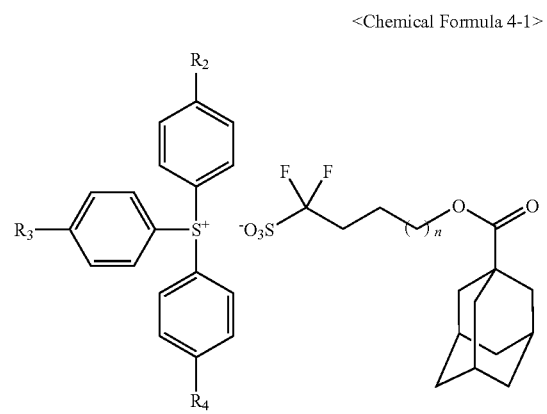

-continued

<Chemical Formula 4-2>

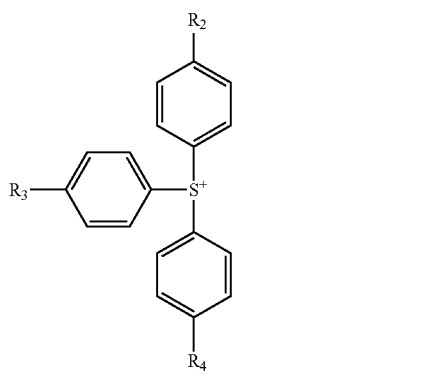

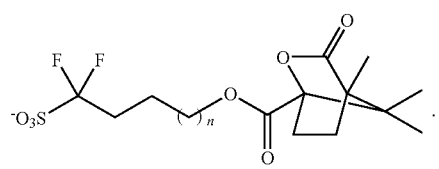

7. A photoresist composition comprising:
about 4% to about 10% by weight of a photoresist resin;
about 0.1% to about 0.5% by weight of a photoacid generator having a sulfonium-salt cationic group selected from the group consisting of compounds represented by the following Chemical Formulas 1, 2, 3 and 4, and a sulfonium-salt anionic group represented by the following Chemical Formula 5 and containing a carboxyl group as a hydrophilic site, wherein $R_1$, $R_2$, $R_3$ and $R_4$ independently represent a hydrogen atom or an alkyl group having 1 to 5 carbon atoms, n represents a natural number of 1 to 3, and X represents one selected from the group consisting of a cyclic group having 4 to 10 carbon atoms, an adamantyl group and a cycloheptyl group containing an oxygen atom; and <Chemical Formula 1>

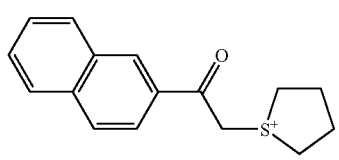

<Chemical Formula 2>

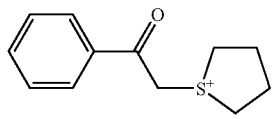

<Chemical Formula 3>

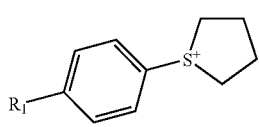

-continued

<Chemical Formula 4>

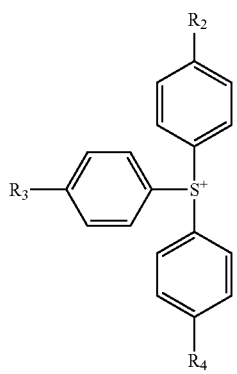

<Chemical Formula 5>

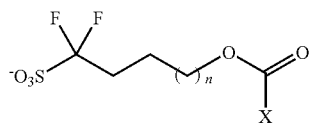

a remainder of a solvent.

8. The photoresist composition of claim 7, wherein the photoacid generator is capable of reacting with light to form a sulfonic acid represented by the following Chemical Formula 6, wherein n represents a natural number of 1 to 3, and X represents one selected from the group consisting of a cyclic group having 4 to 10 carbon atoms, an adamantyl group and a cycloheptyl group containing an oxygen atom <Chemical Formula 6>

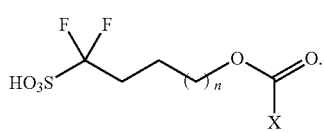

9. The photoresist composition of claim 7, wherein the photoacid generator is represented by the following Chemical Formula 1-1 or Chemical Formula 1-2, wherein n represents a natural number of 1 to 3

<Chemical Formula 1-1>

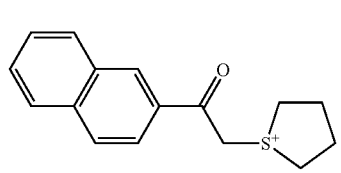

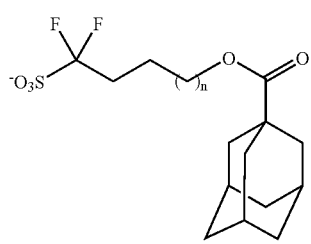

-continued

<Chemical Formula 1-2>

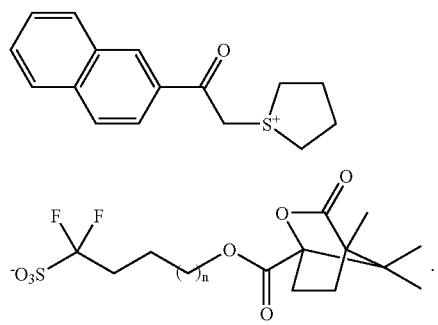

10. The photoresist composition of claim 7, wherein the photoacid generator is represented by the following Chemical Formula 2-1 or Chemical Formula 2-2, wherein n represents a natural number of 1 to 3

<Chemical Formula 2-1>

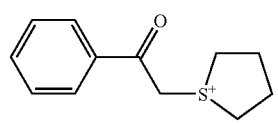

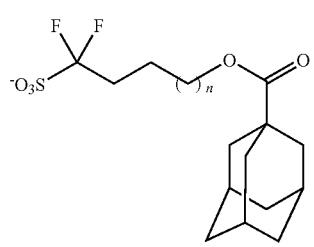

<Chemical Formula 2-2>

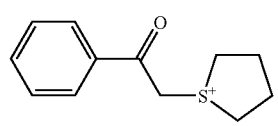

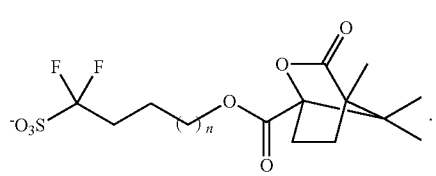

11. The photoresist composition of claim 7, wherein the photoacid generator is represented by the following Chemical Formula 3-1 or Chemical Formula 3-2, wherein n represents a natural number of 1 to 3, and $R_1$ represents a hydrogen atom or an alkyl group having 1 to 3 carbon atoms <Chemical Formula 3-1>

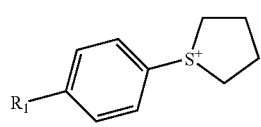

-continued

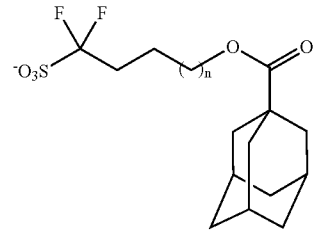

<Chemical Formula 3-2>

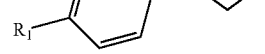

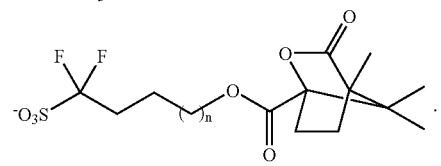

12. The photoresist composition of claim 7, wherein the resin includes a methacrylate repeat unit having a lactone group and a methacrylate repeat unit having an adamantyl group.

13. A method of forming pattern, the method comprising:
coating a photoresist composition on an object layer to form a photoresist film, the photoresist composition comprising about 4% to about 10% by weight of a photoresist resin, about 0.1% to about 0.5% by weight of a photoacid generator having a sulfonium-salt cationic group selected from the group consisting of compounds represented by the following Chemical Formulas 1, 2, 3 and 4, and a sulfonium-salt anionic group represented by the following Chemical Formula 5 and containing a carboxyl group as a hydrophilic site, wherein $R_1$, $R_2$, $R_3$ and $R_4$ independently represent a hydrogen atom or an alkyl group having 1 to 5 carbon atoms, n represents a natural number of 1 to 3, and X represents one selected from the group consisting of a cyclic group having 4 to 10 carbon atoms, an adamantyl group and a cycloheptyl group containing an oxygen atom, and a remainder of a solvent;

<Chemical Formula 1>

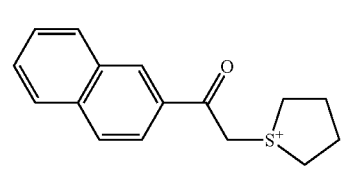

<Chemical Formula 2>

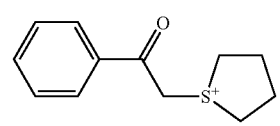

<Chemical Formula 3>

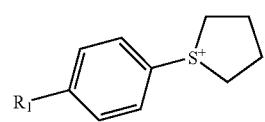

-continued
<Chemical Formula 4>
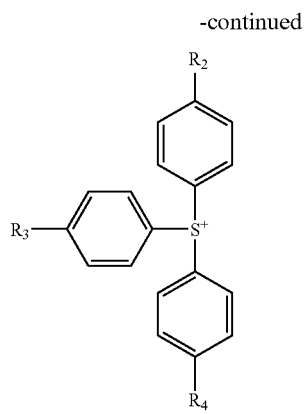
-continued
<Chemical Formula 5>
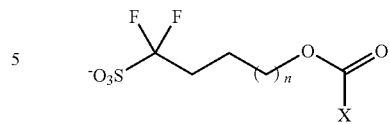
exposing the photoresist film to light;
developing the photoresist film to form a photoresist pattern; and
etching an exposed portion of the object layer by using the photoresist pattern as an etching mask to form an object layer pattern.
* * * * *